United States Patent [19]

Boller et al.

[11] 4,058,478

[45] * Nov. 15, 1977

[54] LIQUID CRYSTAL ESTERS

[75] Inventors: Arthur Boller, Binningen; Hanspeter Scherrer, Therwil, both of Switzerland

[73] Assignee: Hoffmann-La Roche Inc., Nutley, N.J.

[*] Notice: The portion of the term of this patent subsequent to Sept. 21, 1993, has been disclaimed.

[21] Appl. No.: 606,156

[22] Filed: Aug. 20, 1975

Related U.S. Application Data

[62] Division of Ser. No. 334,291, Feb. 21, 1973, Pat. No. 3,923,857.

[30] Foreign Application Priority Data

Feb. 23, 1972 Switzerland .................... 2586/72
Jan. 23, 1973 Switzerland ..................... 920/73

[51] Int. Cl.$^2$ ................... C09K 3/34; G02F 1/13
[52] U.S. Cl. .................. 252/299; 252/63.7; 252/300; 252/408; 350/150; 350/160 LC
[58] Field of Search ........... 252/299, 408, 300, 63.7; 350/160 LC, 150

[56] References Cited

U.S. PATENT DOCUMENTS

| 3,795,436 | 3/1974 | Boller et al. | 252/299 |
| 3,796,479 | 3/1974 | Helfrich et al. | 252/299 |
| 3,815,972 | 6/1974 | Hsieh | 252/299 |
| 3,923,857 | 12/1975 | Boller et al. | 252/299 |
| 3,963,311 | 6/1976 | Boller et al. | 252/299 |
| 3,981,817 | 9/1976 | Boller et al. | 252/299 |

FOREIGN PATENT DOCUMENTS

| 2,024,269 | 12/1971 | Germany | 252/299 |
| 2,234,522 | 1/1973 | Germany | 252/299 |
| 2,327,036 | 12/1973 | Germany | 252/299 |
| 4,978,683 | 7/1974 | Japan | 252/299 |

OTHER PUBLICATIONS

Schadt; M., J. Chem. Phys., vol. 56, No. 4, pp. 1494–1497 (2/15/72).
Boller; A. et al., Proc. of the IEEE, pp. 1002–1003 (Aug. 1972).

*Primary Examiner*—Benjamin R. Padgett
*Assistant Examiner*—T. S. Gron
*Attorney, Agent, or Firm*—Samuel L. Welt; Bernard S. Leon; William G. Isgro

[57] ABSTRACT

Liquid crystal substances or compounds of the formula

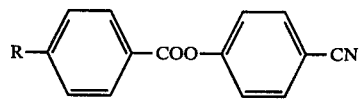

I wherein R is as hereinafter set forth, as well as compositions and electro-optical apparatuses containing them are described.

10 Claims, No Drawings

LIQUID CRYSTAL ESTERS

This is a division of application Ser. No. 334,291, filed Feb. 21, 1973, now U.S. Pat. No. 3,923,857.

BRIEF SUMMARY OF THE INVENTION

The invention relates to liquid crystalline esters of the formula

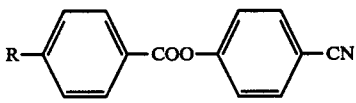

wherein R is lower alkyl of 4 to 8 carbon atoms or lower alkoxy of 5 to 8 carbon atoms.

In another aspect, the invention relates to nematic mixtures for electro-optical uses containing the esters of the invention and to the preparation thereof. In still another aspect, the invention relates to dielectrics for electro-optical uses and to the preparation thereof. In yet another aspect, the invention relates to an optical cell comprising as a liquid crystal means one or more esters of the invention.

DETAILED DESCRIPTION OF THE INVENTION

The liquid crystalline esters provided by the invention are compounds of the formula

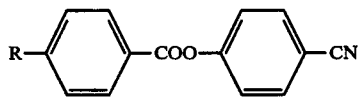

wherein R is straight-chain alkyl of 4 to 8 carbon atoms or straight-chain alkoxy of 5 to 8 carbon atoms.

The nematic liquid crystal compounds of formula I possess, in the liquid crystalline state, a positive anisotropy of the dielectric constants ($\epsilon_{\|} > \epsilon_{\perp}$, $\epsilon_{\|}$ signifies the dielectric constant along the longitudinal axis of the molecule and $\epsilon_{\perp}$ signifies the dielectric constant perpendicular thereto).

In an electric field, the nematic liquid crystals of the invention orient themselves (because $\epsilon_{\|} > \epsilon_{\perp}$) with the direction of their largest dielectric constant, (i.e., with their longitudinal axes) parallel to the field direction. This effect is employed, inter alia, in the interaction between embedded molecules and liquid crystalline molecules (guest-host interaction) described by J. H. Heilmeier and L. A. Zanoni [Applied Physics Letters 13, 91 (1968)]. A further interesting application of the dielectric field orientation exists in the rotation cell discovered by M. Schadt and W. Helfrich [Applied Physics Letters 18, 127 (1971)].

The electro-optical rotation cell of Schadt et al., supra, comprises essentially a condenser having transparent electrodes whose dielectric is formed from a nematic substance or liquid crystal with a dielectric constant of $\epsilon_{\|} > \epsilon_{\perp}$. The longitudinal axes of the molecules of the liquid crystal are arranged in twisted form between the condenser plates in the fieldless state, the twisting structure being defined by the given wall orientation of the molecules. After the application of an electrical potential to the condenser plates, the molecules adjust themselves with their longitudinal axes in the field direction (i.e., perpendicular to the surface of the plates), whereby linear polarized light is no longer rotated in the dielectric (the liquid crystal is uniaxially perpendicular to the surface of the plates). This effect is reversible and can be used for electrically controlling the optical transmissivity of the condenser.

In such "light rotation cells" it is very desirable to utilize compounds as dielectrics which possess a low melting point and slight viscosity. The compounds previously used for this purpose e.g. p-[(p-ethyloxybenzylidene)amino]benzonitrile have the disadvantage of first showing nematic properties at relatively high temperatures so that electro-optical apparatuses provided with such liquid crystals have to be heated and possibly thermostatted. Further, said compounds possess a high viscosity which, for example, leads to considerable disadvantage in electro-optical apparatuses in that operation thereof requires relatively large voltages and long response times. Unexpectedly, it has now been discovered that the compounds of formula I of the invention possess liquid crystalline properties which correspond to the foregoing requirements. They exhibit not only the necessary large or strong positive anisotropy of the dielectric constants but also individually or in the form of mixtures with one another or with other nematic or non-nematic substances, they are liquid crystalline and exhibit slight viscosity at relatively low temperature. The operation of electro-optical devices is therefore possible with lower voltage and the susceptibility to rearrangement is shorter. An advantage of the compounds of formula I over compounds formerly used for their purpose is their substantially greater stability in view of which they can be handled more conveniently. A further advantage of the compounds of formula I comprises the fact that they form colorless, milky-white nematic phases.

The compounds of formula I are preferably used in the form of mixtures with one another or with other nematic or non-nematic substances. Advantageously, binary or ternary mixtures can be formed. Mixtures whose comosition corresponds to a eutectic are especially preferred.

Preferred binary mixtures contain the components in a molar ratio from about 1 : 10 to about 10 : 1.

More preferred mixtures comprise: p-n-heptylbenzoic acid p'-cyanophenyl ester with p-n-butylbenzoic acid p'-cyanophenyl ester or p-n-pentylbenzoic acid p'-cyanophenyl ester in a molar ratio of 2:1; p-n-octylbenzoic acid p'-cyanophenyl ester with p-n-butylbenzoic acid p'-cyanophenyl ester of p-n-hexylbenzoic acid p'-cyanophenyl ester in a molar ratio of 2:1; or p-n-hexylbenzoic acid p'-cyanophenyl ester with p-n-butylbenzoic acid p'-cyanophenyl ester in a molar ratio of 2:1.

The compounds of formula I of the invention can be prepared in accordance with the processes hereinafter set forth as follows:

a. reacting a compound of the formula

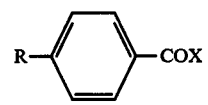

wherein R is as hereinbefore described, and X is a leaving atom or group,
with p-hydroxybenzonitrile; or
b. dehydrating a compound of the formula

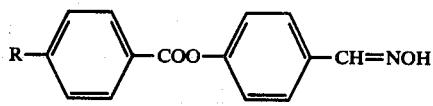

wherein R is as hereinafter described; or
c. reacting a compound of the formula

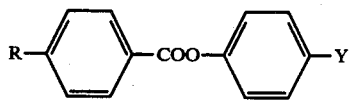

wherein R is as hereinbefore described, and Y is halogen or arylsulfonyloxy,
with cuprous cyanide or sodium cyanide; or
d. dehydrating a compound of the formula

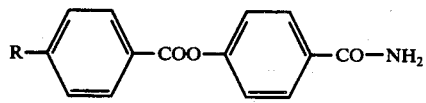

wherein R is as hereinbefore described; or
e. diazotizing a compound of the formula

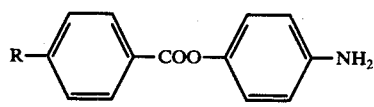

wherein R is as hereinbefore described,
and reacting the diazonium salt so obtained with cuprous cyanide.

The leaving atom or group denoted by X in formula II can be halogen, for example, chlorine or bromine, lower alkoxy of 1 to 7 carbon atoms, preferably methoxy or ethoxy; lower alkanoyloxy of 1 to 7 carbon atoms, preferably formyloxy or acetoxy; aryl-(lower alkoxy)-, preferably phenyl-(lower alkoxy) of 1 to 7 carbon atoms, such as benzyloxy; aryl-(lower alkanoyloxy)- preferably phenyl-(lower alkanoyloxy)- of 1 to 7 carbon atoms, such as benzoyloxy; lower alkylsulfonyloxy, preferably mesyloxy; or arylsulfonyloxy, preferably tosyloxy.

In process embodiment (a) of the invention, a compound of formula II is reacted with p-hydroxybenzonitrile. The reaction is expediently carried out in an inert organic solvent, for example, an ether, such as diethyl ether, tetrahydrofuran or the like, dimethylformamide, benzene, toluene, cyclohexane or carbon tetrachloride.

In the compounds of formula II, X preferably is halogen, for example, chlorine. In order to bind the hydrogen halide released during the reaction, an acid binding agent is conveniently utilized in the reaction mixture. Suitable acid binding agents comprise tertiary amines, pyridine, or the like. The acid binding agent is preferably present in a large excess so that it can serve simultaneously as a solvent and acid binding agent. The temperature and pressure are not critical aspects of the reaction. However, the reaction is generally carried out at atmospheric pressure and at a temperature in the range of between about room temperature and the boiling temperature of the reaction mixture.

The compounds of formula II wherein X is chlorine can be prepared by reacting a corresponding benzoic acid with thionyl chloride. Thereafter, it is not necessary to isolate the resulting compound of formula II from the mixture in which it is prepared prior to the reaction with p-hydroxybenzonitrile.

In process embodiment (b) of the invention, a compound of formula III is dehydrated. The dehydration is conveniently carried out using acetic anhydride or anhydrous sodium acetate in glacial acetic acid. The dehydration is carried out at the reflux temperature of the reaction mixture. The pressure is not critical, but the dehydration is advantageously carried out at atmospheric pressure.

The compounds of formula III can be prepared by reacting a compound of formula II with p-hydroxybenzaldehyde and reacting the resulting ester with hydroxylamine. A compound of formula III so-obtained need not be isolated from the mixture in which it is prepared, but can be dehydrated in situ.

In process embodiment (c) of the invention, a compound of formula IV is reacted, for example, with cuprous cyanide or sodium cyanide. This reaction is expediently carried out in an inert organic solvent, for example, ethyleneglycol, tetrahydrofuran, dimethylformamide, dimethylsulfoxide, pyridine or acetonitrile. Temperature and pressure are not critical aspects in this reaction. It is expedient to carry out the reaction at atmospheric pressure and at a temperature in the range of between about room temperature and about the boiling temperature of the reaction mixture.

In the compounds of formula IV, X preferably is halogen, for example, bromine. Such compounds can be prepared, for example, by reacting a compound of formula II with p-bromophenol. The resulting compound need not be isolated from the reaction mixture, but can be reacted in situ with cuprous cyanide or sodium cyanide.

In process embodiment (d) of the invention, a compound of formula V is dehydrated. The dehydration can be carried out by boiling a compound of formula V with acetic anhydride in glacial acetic acid or by utilizing phosphorus pentoxide, phosphorus pentachloride, phosphorus oxychloride, thionyl chloride, or the like. The dehydration is preferably carried out in the absence of a solvent but can be carried out in a solvent, for example, benzene, dimethylformamide, pyridine, ethylene dichloride, or the like. The dehydration is advantageously carried out at the reflux temperature of the mixture or the boiling point of the product. Conveniently, the dehydration is carried out at atmospheric pressure or at a reduced pressure.

The compounds of formula V can be prepared by reacting a compound of formula II with p-hydroxybenzoic acid, converting the resulting product into an acid chloride and treating this with ammonia. The resulting compound of formula V need not be isolated from the mixture in which it is prepared, but can be dehydrated in situ.

In process embodiment (e) of the invention, a compound of formula VI is utilized as the starting material. It is diazotized and the resulting diazonium salt is subjected to a Sandmeyer reaction. The diazotization is carried out in water at a temperature in the range of from about 0° to 5° C. with the addition of hydrochloric acid and sodium nitrite. The diazonium chloride obtained is then subjected to a Sandmeyer reaction. The latter reaction is conveniently carried out utilizing a solution of, for example, cuprous cyanide or a complex salt thereof. The reaction is carried out at a temperature in the range of between about 0° and about 100° C., preferably in the range of from about 70° to about 80° C. Pressure is not critical, but the reaction is advantageously carried out at atmospheric pressure.

The compounds of formula VI can be prepared by reacting a compound of formula II with N-benzylidene-p-hydroxyaniline and subsequent cleavage of the resulting Schiffs' base with an aqueous mineral acid.

The physical properties of the nematic compounds of formula I provided by the invention are set forth in the following Table I:

TABLE I

R—⟨phenyl⟩—COO—⟨phenyl⟩—CN

| | R | Melting Point | Clearing Point |
|---|---|---|---|
| A | n-butyl | 67° C. | (41.5° C.)* |
| B | n-pentyl | 60.5° C. | (56.5° C.)* |
| C | n-hexyl | 45° C. | 48° C. |
| D | n-heptyl | 44° C. | 56.5° C. |
| E | n-octyl | 46.5° C. | 53.5° C. |
| F | n-pentyloxy | 85° – 85.5° C. | (76.5° – 77° C.)* |
| G | n-hexyloxy | 71° C. | 82° C. |
| H | n-heptyloxy | 71.5° C. | 80° C. |
| I | n-octyloxy | 73° – 74° C. | 83° C. |

*monotrope clearing point

The compounds of formula I are preferably used in the form of mixtures with one another. Mixtures which correspond to a eutectic are especially preferred.

Exemplary of such mixtures are those set forth in following Table II:

TABLE II

| Mixture | Melting Point | Clearing Point |
|---|---|---|
| 67% p-n-heptylbenzoic acid p'-cyanophenyl ester + 33% p-n-butylbenzoic acid p'-cyanophenyl ester | 24° – 26° C. | 50° C. |
| 67% p-n-heptylbenzoic acid p'-cyanophenyl ester + 33% p-n-pentylbenzoic acid p'-cyanophenyl ester | 30° – 30.5° C. | 56° C. |
| 67% p-n-octylbenzoic acid p'-cyanophenyl ester + 33% p-n-butylbenzoic acid p'-cyanophenyl ester | 22° – 24° C. | 48.5° C. |
| 67% p-n-octylbenzoic acid p'-cyanophenyl ester + 33% p-n-hexylbenzoic acid p'-cyanophenyl ester | 22° – 23° C. | 51° C. |
| 67% p-n-hexylbenzoic acid p'-cyanophenyl ester + 33% p-n-butylbenzoic acid p'-cyanophenyl ester | 22° – 23° C. | 45° – 45.5° C. |

The compounds of formula I can also be used in the form of mixtures with other nematic or non-nematic substances, for example, with Schiffs' bases of the formula

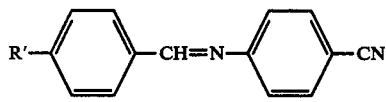

VII wherein R' is a straight-chain lower alkyl of 2 to 8 carbon atoms, straight-chain alkoxy of 4 to 7 carbon atoms, or straight-chain lower alkanoyloxy of 2 to 8 carbon atoms.

The Schiffs' bases of formula VII wherein R' is a straight-chain lower alkyl of 2 to 8 carbon atoms are new and can be prepared, for example, by reacting a compound of the formula

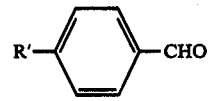

VIII wherein R' is a straight-chain lower alkyl of 2 to 8 carbon atoms,
with p-aminobenzonitrile.

The Schiffs' bases of formula VIII wherein R' is straight-chain lower alkoxy or straight-chain lower alkanoyloxy are known compounds.

The following Examples further illustrate the invention. All temperatures are in degrees Centigrade, unless otherwise mentioned.

EXAMPLE 1

Preparation of p-n-butylbenzoic acid p'-cyanophenyl ester 5.6 g. of p-n-butylbenzoic acid chloride in 12 ml. of absolute benzene are added to 3.1 g. of p-hydroxybenzonitrile in 25 ml. of absolute pyridine. The mixture is stirred overnight at room temperature and subsequently for an additional 2 hours at 50° C. After cooling, the mixture is extracted with ether and the extract washed with dilute hydrochloric acid and water, whereby there are finally obtained 9 g. of crude p-n-butylbenzoic acid p'-cyanophenyl ester. This product is dissolved in toluene and chromatographed on 250 g. of silica gel. From the uniform fraction on the thin-layer there are obtained, after recrystallization from hexane, 4 g. of p-n-butylbenzoic acid p'-cyanophenyl ester, having a melting point of 67° C. and a monotrope clearing point of 41.5° C. The nuclear magnetic resonance and infrared spectra correspond to the expected structure.

The starting material, i.e., p-n-butylbenzoic acid chloride, can be prepared as follows:

50 g. of p-n-butylbenzoic acid are dissolved in 150 ml. of thionyl chloride, and the mixture is boiled at reflux for 1 hour. The excess thionyl chloride is then removed at normal pressure and the p-n-butylbenzoic acid chloride distilled under a high vacuum. The obtained p-n-butylbenzoic acid chloride has a boiling point of 100° – 105° C/2–5 mm.

EXAMPLE 2

Preparation of p-n-pentylbenzoic acid p'-cyanophenyl ester 3.1 g. of p-hydroxybenzonitrile are dissolved in 40 ml. of absolute pyridine. Then 6 g. of p-n-pentylbenzoic acid chloride in 20 ml. of benzene are added dropwise at room temperature and the mixture is subsequently stirred overnight. After warming for a short period, the mixture is worked up as described in Example 1, whereby there are obtained 7.5 g. of crude ester. The latter is chromatographed on silica gel using toluene-/acetone (19:1). From the uniform fraction there are obtained, after recrystallization from hexane, 2.6 g. of p-n-pentylbenzoic acid p'-cyanophenyl ester having a melting point of 60.5° C. and a monotrope clearing point of 56.5° C.

The starting material, i.e., p-n-pentylbenzoic acid chloride, can be prepared as follows:

15 g. of p-n-pentylbenzoic acid are dissolved in 100 ml. of thionyl chloride, and the mixture is boiled at reflux for 1 hour. The excess thionyl chloride is then removed by distillation and the desired acid chloride distilled under a high vacuum. The obtained p-n-pentylbenzoic acid chloride has a boiling point of 104° C/2 mm.

EXAMPLE 3

Preparation of p-n-hexylbenzoic acid p'-cyanophenyl ester 1.4 g. of p-hydroxybenzonitrile in 25 ml. of absolute pyridine and 2.9 g. of p-n-hexylbenzoic acid chloride in 23 ml of absolute benzene are mixed together, stirred overnight at room temperature and subsequently for an additional 2 hours at 50° C. The cooled reaction mixture is poured on to ice-water and then extracted with ether. The mixture is washed with dilute hydrochloric acid, dilute sodium hydroxide and finally with water until neutral. After drying and concentration of the solution, there are obtained 3.7 g. of crude product. Said product is chromatographed on silica gel using toluene/acetone (19:1), whereby there are finally obtained 1.4 g. of p-n-hexylbenzoic acid p'-cyanophenyl ester having a melting point of 45° C. and a clearing point of 48° C.

The starting material, i.e., p-n-hexylbenzoic acid chloride, can be prepared as follows:

9.4 g. of p-n-hexylbenzoic acid and 50 ml. of thionyl chloride are mixed together and warmed for 1 hour at 80° C. The excess thionyl chloride is then removed by distillation at normal pressure and the p-n-hexylbenzoic acid chloride is removed by distillation under a high vacuum. The obtained p-n-hexylbenzoic acid chloride has a boiling point of 110° C/0.05 mm.

EXAMPLE 4

Preparation of p-n-heptylbenzoic acid p'-cyanophenyl ester 6.6 g. of p-n-heptylbenzoic acid chloride are dissolved in 25 ml. of absolute benzene and added dropwise to 3 g. of p-hydroxybenzonitrile in 50 ml. of absolute pyridine. The reaction mixture is stirred overnight at room temperature and then for an additional 2 hours at 50° C. After cooling, ice-water is added and the product is extracted with ether. The ether extract is washed with dilute hydrochloric acid, dilute sodium hydroxide and water, whereby there are finally obtained 7.6 g. of crude p-n-heptylbenzoic acid p'-cyanophenyl ester. This product is chromatographed on 300 g. of silica gel and eluted with hexane/ether (4:1). After recrystallization from hexane, 6.0 g. of the desired p-n-heptylbenzoic acid p'-cyanophenyl ester are obtained, having a melting point of 44° C. and a clearing point of 56.5° C.

The starting material, i.e., p-n-heptylbenzoic acid chloride, can be prepared as follows:

15 g. of p-n-heptylbenzoic acid and 100 ml. of thionyl chloride are boiled at reflux until the evolution of gas has terminated. The excess thionyl chloride is then removed by distillation at normal pressure and the p-n-heptylbenzoic acid chloride is distilled under a high vacuum, whereby 13.2 g. of p-n-heptylbenzoic acid chloride, having a boiling point of 165°-167° C./5mm. are obtained.

EXAMPLE 5

Preparation of p-n-octylbenzoic acid p'-cyanophenyl ester 7 g. of p-n-octylbenzoic acid chloride in 25 ml. of absolute benzene are added dropwise to 3 g. of p-hydroxybenzonitrile in 50 ml. of absolute pyridine. The mixture is then stirred overnight at room temperature and for an additional 2 hours at 50° C. The reaction mixture is poured on to ice-water and the product isolated as described in Example 4. 8.7 g. of crude ester are chromatographed on silica gel using benzene. After recrystallization from hexane, there are obtained 5.2 g. of pure p-n-octylbenzoic acid p'-cyanophenyl ester having a melting point of 46.5° C and a clearing point of 53.5° C.

The starting material, i.e., p-n-octylbenzoic acid chloride, can be prepared as follows:

20 g. of p-n-octylbenzoic acid and 100 ml. of thionyl chloride are boiled at reflux for 1 hour. The excess thionyl chloride is removed by distillation at normal pressure. The residue is mixed with absolute toluene and concentrated under vacuum. The obtained crude p-n-octylbenzoic acid chloride can be used without further purification.

EXAMPLE 6

Preparation of p-n-butylbenzoic acid p'-cyanophenyl ester 4.5 g. of p-hydroxybenzaldehyde are dissolved in 50 ml. of pyridine. 8 g. of p-n-butylbenzoic acid chloride in 25 ml. of benzene are added dropwise thereto at room temperature. The mixture is stirred overnight at room temperature and subsequently for an additional 2 hours at 50° C. The mixture is then poured on to ice-water and extracted with ether. The ether extract is washed with water, dilute hydrochloric acid and water, whereby there are finally obtained, after drying and concentration of the solution, 10.2 g. of crude p-n-butylbenzoic acid p'-cyanophenyl ester. 8.2 g. of the crystalline ester are obtained after recrystallization from ether/hexane. 8 g. of this ester are boiled at reflux for 16 hours with 2.85 g.. of hydroxylamine hydrochloride and 4.5 g. of anhydrous sodium acetate in 100 ml. of glacial acetic acid. The mixture is cooled, the major portion of glacial acetic acid is removed by distillation under vacuum, water added to the residue and the product extracted with ether. From the ether extract there are obtained, after washing with water and drying with sodium sulfate, 7.0 g. of crude product. This product is chromatographed on silica gel using benzene. From the uniform fractions there is obtained, after recrystallization from hexane, p-n-butylbenzoic acid p'-cyanophenyl ester which is identical with that obtained in Example 1.

EXAMPLE 7

Preparation of p-n-octylbenzoic acid p'-cyanophenyl ester 3.7 g. of p-n-octylbenzoic acid p'-bromophenyl ester are boiling at reflux with 1.1 g. of cuprous cyanide in 5 ml. of dimethylformamide. The reaction mixture is then poured on to 2 ml. of ethylenediamine and 6 ml. of water, shaken vigorously for 5 minutes and then extracted twice with benzene. The organic extracts are washed again with ethylenediamine in water and then several times with water. There are obtained 1.9 g. of crystalline crude product still containing a small amount of starting material which is then separated by chromatography on silica gel using toluene. The p-n-octylbenzoic acid p'-cyanophenyl ester obtained after recrystallization has a melting point of 46.5° C. and a clearing point of 54° C. and is identical with the product obtained in Example 5.

The starting material, i.e., p-n-octylbenzoic acid p'-bromophenyl ester, can be prepared as follows:

4.5 g. of p-bromophenol are dissolved in 50 ml. of absolute pyridine and mixed with 7 g. of p-n-octylbenzoic acid chloride in 25 ml. of absolute benzene. The mixture is subsequently stirred overnight at room temperature and then poured into ice-water and extracted with ether. The organic phase is washed with dilute hydrochloric acid, dilute sodium hydroxide and water, dried over sodium sulfate and concentrated, whereby there are obtained 8.4 g. of p-n-octylbenzoic acid p'-bromophenyl ester which is practically pure on thin-layer.

EXAMPLE 8

Preparation of p-n-hexyloxybenzoic acid p'-cyanophenyl ester 2 g. of p-hydroxybenzonitrile are dissolved in 5 ml. of absolute pyridine. A solution of 4 g. of p-n-hexyloxybenzoic acid chloride in 2 ml. of absolute benzene is added at room temperature to the resulting solution. The mixture is stirred overnight at room temperature, then taken up in ether and the ether phase washed successively with dilute hydrochloric acid, dilute sodium hydroxide and distilled water. After drying and concentration, there are obtained 4.9 g. of crude product which is recrystallized twice from ethanol to yield 4.3 g. of p-n-hexyloxybenzoic acid p'-cyanophenyl ester having a melting point of 71° C. and a clearing point of 82° C.

The p-n-hexyloxybenzoic acid chloride starting material can be prepared by boiling p-n-hexyloxybenzoic acid with thionyl chloride followed by distillation at 130° C/0.1 mm.

The following Example illustrates the preparation of a Schiffs' base of formula VII:

EXAMPLE A

Preparation of p-[(p-ethylbenzyliden)amino]benzonitrile

A mixture of 5.9 g. of p-aminobenzonitrile and 6.7 g. of p-ethylbenzaldehyde is gassed with nitrogen in 100 ml. of benzene after the addition of 150 mg. of p-toluenesulfonic acid and the mixture is heated at reflux for 1 hour (bath temperature 120° C.). The water formed is removed by means of a water separator. During an additional hour, the benzene which condensed in the reflux condenser is led back into the reaction vessel via a layer of 50 g. of aluminum oxide (activity I). After cooling, 2 g. of solid potassium carbonate are added. Then, the mixture is filtered and the filtrate freed from a solvent under vacuum at 50° C. (bath temperature), whereby there remains 11.5 g. of a yellow oil which crystallizes upon cooling. Purification is carried out by several recrystallizations from isopropanol to a constant melting point and until by-products can no longer be observed by gas chromatogram. The pure p-[(p-ethylbenzyliden)-amino]benzonitrile melts at 76.2°-77.0° C. and is liquid crystalline upon cooling 63.0°-59.7° C.; U.V. (ethanol); ε = 25800 (shoulder at 316 nm). The nuclear magnetic resonance, mass spectrum, infrared and microanalysis confirm the structure of the product.

We claim:

1. A nematic composition which comprises two or more compounds of the formula

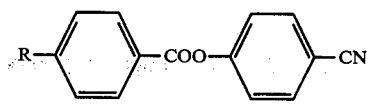

wherein R is straight-chain lower alkyl of 4 to 8 carbon atoms.

2. A nematic composition in accordance with claim 1, which comprises a mixture of p-n-heptylbenzoic acid p'-cyanophenyl ester and p-n-butylbenzoic acid p'-cyanophenyl ester.

3. A nematic composition in accordance with claim 1, which comprises a mixture of p-n-heptylbenzoic acid p'-cyanophenyl ester and p-n-pentylbenzoic acid p'-cyanophenyl ester.

4. A nematic composition in accordance with claim 1, which comprises a mixture of p-n-octylbenzoic acid p'-cyanophenyl ester and p-n-butylbenzoic acid p'-cyanophenyl ester.

5. A nematic composition in accordance with claim 1, which comprises a mixture of p-n-octylbenzoic acid p'-cyanophenyl ester and p-n-hexylbenzoic acid p'-cyanophenyl ester.

6. A nematic composition in accordance with claim 1, which comprises a mixture of p-n-hexylbenzoic acid p'-cyanophenyl ester and p-n-butylbenzoic acid p'-cyanophenyl ester.

7. A nematic composition which comprises an ester of the formula

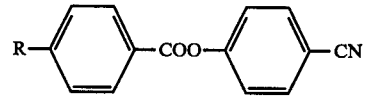

wherein R is straight-chain lower alkyl of 4 to 8 carbon atoms,
or mixtures thereof and one or more nematic compounds having a positive anisotropy.

8. A nematic composition which comprises an ester of the formula

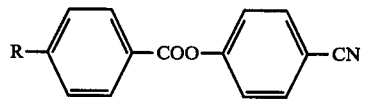

wherein R is straight-chain lower alkyl of 4 to 8 carbon atoms, or mixtures thereof, and a Schiffs' base of the formula

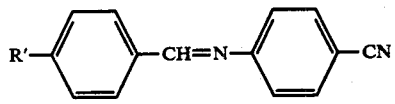

wherein R' is straight-chain lower alkyl of 2 to 8 carbon atoms, straight-chain lower alkoxy of 4 to 7 atoms, or straight-chain lower alkanoyloxy of 2 to 8 carbon atoms.

9. A dielectric for electro-optical purposes which comprises two or more compounds

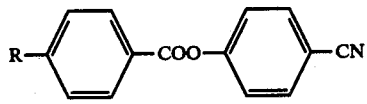

wherein R is straight-chain lower alkyl of 4 to 8 carbon atoms,
or mixtures thereof.

10. A dielectric for electro-optical purposes, which comprises a nematic ester of the formula

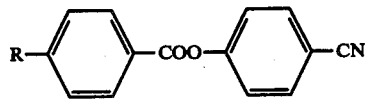

wherein R is straight-chain lower alkyl of 4 to 8 carbon atoms,
or mixtures thereof and one or more nematic compounds having positive anisotropy.

* * * * *

UNITED STATES PATENT AND TRADEMARK OFFICE
CERTIFICATE OF CORRECTION

PATENT NO. : 4,058,478
DATED : November 15, 1977
INVENTOR(S) : Arthur Boller et al.

It is certified that error appears in the above-identified patent and that said Letters Patent are hereby corrected as shown below:

Column 11, claim 9, line 21, after "comprises two or more compounds" insert — of the formula

Signed and Sealed this

Twenty-seventh Day of February 1979

[SEAL]

Attest:

RUTH C. MASON
Attesting Officer

DONALD W. BANNER
Commissioner of Patents and Trademarks